United States Patent
Derr et al.

(10) Patent No.: US 9,367,915 B2
(45) Date of Patent: *Jun. 14, 2016

(54) METHOD AND SYSTEM FOR ANALYZING OPTICAL COHERENCE TOMOGRAPHY (OCT) RESULTS USING COLOR REFLECTIVITY DISCRETIZATION ANALYSIS

(71) Applicant: DIOPSYS, INC., Pine Brook, NJ (US)

(72) Inventors: Peter Derr, East Windsor, NJ (US); Alberto Gonzalez, Pine Brook, NJ (US); Laurie Cox, Rockaway, NJ (US)

(73) Assignee: Diopsys, Inc., Pine Brook, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/338,059

(22) Filed: Jul. 22, 2014

(65) Prior Publication Data

US 2014/0334704 A1 Nov. 13, 2014

Related U.S. Application Data

(63) Continuation of application No. 13/188,193, filed on Jul. 21, 2011, now Pat. No. 8,787,645.

(60) Provisional application No. 61/366,485, filed on Jul. 21, 2010.

(51) Int. Cl.
G06K 9/00 (2006.01)
G06T 7/00 (2006.01)
G06K 9/46 (2006.01)
G06K 9/62 (2006.01)

(52) U.S. Cl.
CPC ............ *G06T 7/0012* (2013.01); *G06K 9/4652* (2013.01); *G06K 9/6284* (2013.01); *G06T 2207/10101* (2013.01); *G06T 2207/20148* (2013.01); *G06T 2207/30041* (2013.01)

(58) Field of Classification Search
USPC .................................. 382/192–194, 128–134
See application file for complete search history.

(56) References Cited

U.S. PATENT DOCUMENTS

| | | | | |
|---|---|---|---|---|
| 5,421,339 | A * | 6/1995 | Ramanujam et al. | 600/477 |
| 7,515,952 | B2 * | 4/2009 | Balas et al. | 600/476 |
| 8,787,645 | B2 * | 7/2014 | Derr et al. | 382/131 |
| 2001/0031079 | A1 * | 10/2001 | Ryder | 382/141 |
| 2007/0058086 | A1 * | 3/2007 | Yeo et al. | 348/739 |
| 2008/0123922 | A1 * | 5/2008 | Gielen et al. | 382/131 |
| 2008/0123923 | A1 * | 5/2008 | Gielen et al. | 382/131 |
| 2008/0273783 | A1 * | 11/2008 | Toth et al. | 382/131 |
| 2009/0196477 | A1 * | 8/2009 | Cense et al. | 382/131 |
| 2011/0216956 | A1 * | 9/2011 | Bower et al. | 382/131 |
| 2012/0020539 | A1 * | 1/2012 | Derr et al. | 382/131 |

* cited by examiner

*Primary Examiner* — Alex Liew
(74) *Attorney, Agent, or Firm* — Levisohn Berger LLP (57) ABSTRACT

A method of analyzing an OCT image. An OCT image has many differently colored dots. The system detects the number of differently colored dots, quantifies them and performs statistical analyses to determine a likelihood of disease. The different colored dots correspond to different retina cell types and structures.

8 Claims, 5 Drawing Sheets

METHOD AND SYSTEM FOR ANALYZING OPTICAL COHERENCE TOMOGRAPHY (OCT) RESULTS USING COLOR REFLECTIVITY DISCRETIZATION ANALYSIS

RELATED APPLICATIONS

This Application is a continuation of U.S. patent application Ser. No. 13/188,193 filed on Jul. 21, 2011 (to issue as U.S. Pat. No. 8,787,645 on the filing date hereof) and which claims the benefit of U.S. Provisional Patent Appl. Ser. No. 61/366,485 file on Jul. 21, 2010—the contents of which are incorporated by reference herein.

FIELD OF THE INVENTION

The current invention relates to the field of Optical Coherence Tomography (OCT), more specifically to a novel system for analyzing and interpreting OCT images.

BACKGROUND OF THE INVENTION

OCT is an interferometric and spectrometric technique commonly used in the medical field for acquiring micrometer resolution images of biologic tissues. An OCT instrument focuses light on a tissue and reflected light is detected and analyzed. A combination of light reflected from the tissue and a reference light source give rise to an interference and spectrum pattern. Using this process, both, two and three-dimensional images of tissue is generated.

OCT may be used to image any biological tissue or tissue preparation. In the field of ophthalmology, OCT is commonly used for imaging the retina to evaluate a presence of glaucoma. For the detection of glaucoma, the retinal nerve fiber layer (RNFL)—which contains axons of ganglion cells, glial and other support cells—is isolated and measured. RNFL damage typically precedes visual field loss, and as such, detection of RNFL damage may yield early signs of glaucoma or other diseases of the nervous system. Nerve cell loss results in thinning of the RNFL and consequently, one or more areas of RNFL thinning may indicate a presence of glaucoma.

In the current state of the art, RNFL thickness is the only property that is observed by clinicians evaluating for glaucoma. However, testing RNFL thickness without observing or accounting for internal structures of the RNFL may lead to erroneous results and/or diminished sensitivity to glaucoma. If thickness is the only diagnostic metric, an error in the thickness detection algorithm will lead to an erroneous result. In addition, an area of localized thinning may be averaged out in a global RNFL thickness measurement and thereby missed. Furthermore, sectorial defects of the axonal bundles may be missed in the early stages of the diseases—before such defects give rise to detectable RNFL thinning.

The present invention utilizes a conventional OCT image, which contains other diagnostically important information that has heretofore not been recognized or utilized by practitioners and which may be used, either, independently or supplementary to conventional OCT for enhanced detection of glaucoma.

SUMMARY OF THE INVENTION

The current invention is directed to a novel system, which uses a computer with specialized software to quantify various dots distributed through an image of a retina. Each of the dots represents a different biological cell-type and by quantifying the absolute numbers and ratios of the dots, a host of additional diagnostic information may be gleaned from an OCT image.

In addition, the inventive system performs an analysis of the optic disc (lamina cribosa) through the discretization and quantification of dots on radial scans thereof. Dots representing axonal cells and connective supporting tissue are counted to determine whether or not there is reduced reflectivity—a condition consistent with glaucoma.

A typical OCT image will feature at least four different color dots distributed throughout the superior and inferior RNFL. These include red, yellow, green and blue dots. Red and yellow dots (alternatively "hot dots" herein) represent axon and ganglion cells, whereas, green and blue dots (alternatively "cold dots" herein) represent glial and other supporting cells.

In a healthy RNFL, there are more nerve cells than there are supporting cells (hence, more hot dots than cold dots) and axons are more reflective than other cell types due to their perpendicular orientation with respect to the light source. However, in glaucoma disease progression, loss of axons occurs, which translates to a reduced number of hot dots on an OCT image and a smaller spread between hot and cold dots. In a glaucomatous eye, a ratio close to 1 of hot to cold dots may be observed.

The inventive system utilizes specialized software to quantify the absolute number of each of the different color dots, to calculate ratios of hot dots to cold dots and to analyze the ratios to provide an indication of the health of the RNFL. The more closely the ratio approaches 1—the more likely it is that the examined eye is glaucomatous.

This ratio determination is performed globally on an OCT image and also is conducted on a sector-by-sector basis.

In addition to ratio analysis, absolute numbers of each of the dots are compared to an absolute "normal" number stored in a database to determine a probability of disease. The "normal" number is derived by examining OCT images of healthy patients and determining a normal number and distribution of dots. The absolute number comparison also is conducted on a global OCT image and on a sector-by-sector basis.

A similar analysis is conducted on optic nerve radial and parallel scans obtained by way of conventional OCT imaging. Hot and cold dots are counted to determine an absolute number of each and ratios of hot-to-cold dots. Such analysis is performed on each individual radial and parallel slice and on combined slices, which collectively represent the optic disc. Global and slice analysis includes a comparison of absolute numbers of clots with a normative database and an analysis of ratios of hot-to-cold dots.

DETAILED DESCRIPTION OF THE INVENTION

Embodiments of the present invention will now be described with reference to the above-identified Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As described, the invention is directed to a method and a novel software program for evaluating internal structures of the RNFL and performing quantification analyses of these structures. This is done through several novel processes and statistical analyses performed by a computer on conventional OCT raw data and/or OCT images.

Figure 1:
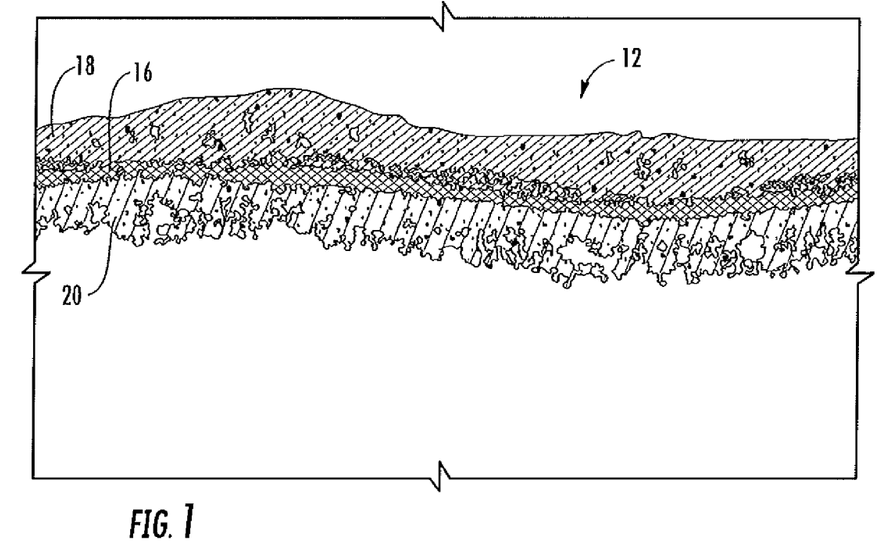
FIG. 1 shows a schematic view of an OCT image of an RNFL segment having focal defects according to an embodiment of the invention.

FIG. 1 shows a schematic view of an OCT test readout 12. As described, in the current state of the art, the thickness of the RNFL layer is measured in order to determine a likelihood of disease. Typical OCT analysis is directed to measuring distances between the upper and lower borders of the upper reflective layer in order to detect any RNFL thinning.

Such analysis, however, does not examine or detect internal defects. In fact, internal defects may precede RNFL thinning and, as such, detecting such defects will allow for earlier detection of ocular disease.

Figure 2:
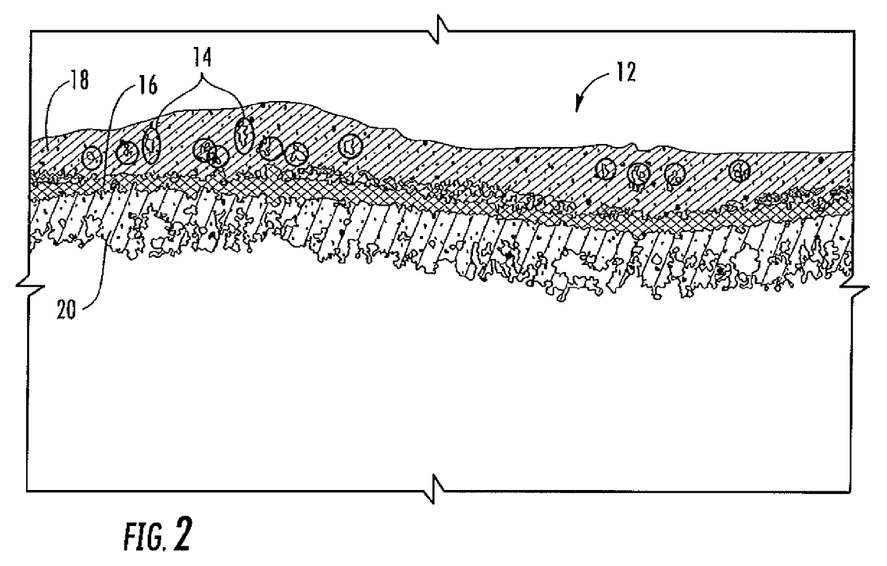
FIG. 2 shows a schematic view of 1 where the focal defects are highlighted.

FIG. 2 shows the OCT image of FIG. 1 where some of the focal defects are highlighted. As shown, there are numerous areas of no color 14 dispersed among the RNFL layer—which are regions of no or diminished reflectivity. As explained, diminished reflectivity may indicate the presence of retinal vessels or cellular loss. Therefore, it is critical to observe these focal defects if glaucoma or other ocular defects are to be detected in their earliest possible stages. In addition, the system and method analyzes and accounts for specific cell types and quantities thereof within the OCT image to similarly detect early signs of disease.

The first step in the inventive analysis is to isolate the RNFL from the rest of the OCT image so that analysis could be conducted thereon. Once the RNFL region is so isolated, the system conducts analysis of the structures as described below.

In one embodiment of the invention, the RNFL is isolated in the following manner: Beginning with an OCT image 12, stored in any of various digital formats, such as raw data, JPEG, TIFF and the like, the native image color is converted into a grayscale image. The software measures the pixel values which comprise the grayscale image and determines an average gray scale shade. The average shade is then set as a threshold value and is used to binarize image pixels to either black or white. An image pixel that is of higher value than that of the threshold value is converted to white, whereas, a pixel having a value below that of the threshold is converted to black. The computer executes this binarization process on a column-by-column basis across an OCT image. Such binarization results in a thin black row 16 at the general midpoint of the image. The image portion 18 immediately above the thin black row is used in the analysis of the RNFL.

As an illustration, assume that <1 0 0 1 1 1 1 0 0 0 1 1 1 0 0 0 1 0> represents a column, whereby the 0s represent black points and the 1s, white points. The column is then grouped as <1 −2 4 −3 3 −3 1 −1> (grouping A) where the negative numbers represent the amount of consecutive black points and the positive numbers represent the amount of consecutive white points. The group is then sorted into descending order to render: <4 3 1 1 −1 −2 −3 −3> (grouping B). The first and second numbers (4 and 3, respectively) represent the two largest groups of consecutive white rows. The software is configured to take the first two numbers of grouping B (representing two largest groups of consecutive white rows—in this example 4 and 3) and then identify their respective positions in grouping A. Once 4 and 3 is identified in grouping A, the software identifies the number that lies in between 4 and 3 (i.e. the number in grouping A that lies directly in between the highest positive numbers identified in grouping B). In this example, number −3 is found to be flanked by 4 and the 3. The group of three consecutive black rows represented by −3 is determined to be the middle black point, which is the dividing row computed for that column. This point is called the middle point.

The software is configured to disregard the lower image portion 20 below the middle point 16 and analyze only the portion there above for RNFL analysis. Referring to grouping A in the above example, −3 represents the midpoint and <1 −2 4> represent the area for RNFL analysis (further assuming that those numbers begin from the top of a column). The group represented by <3 −3 1 −1> is below the middle point and disregarded.

In another embodiment of the invention, image recognition techniques are utilized to isolate the RNFL region for analysis. In this embodiment, an operation to extract the RNFL region is implemented using an operation, such as for example, connected-component labeling, blob extraction, region labeling or such similar operation. Prior to applying such operators one or more digital filtering operations are deployed to reduce noise, such as for example, a Median Filter or the like. Other operations such erosions and dilations may also by employed.

In a preferred embodiment, a Connected Component Labeling Filter (CCL) is utilized to scan an OCT image and group its pixels into components based on pixel connectivity. Once all groups are determined, each pixel is labeled according to the component (e.g. blobs) it was assigned.

Figure 3:
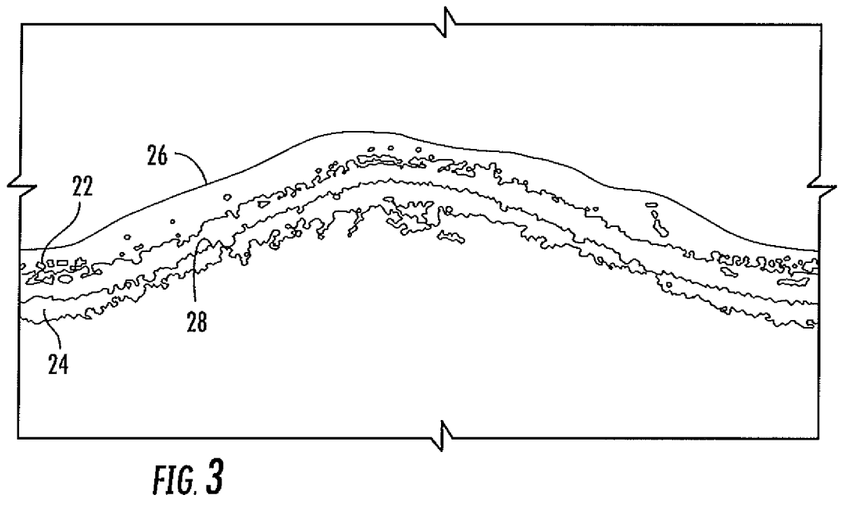
FIG. 3 shows a schematic view of upper and lower reflective regions of an OCT image according to an embodiment of the invention.

Referring to FIG. 3, in an OCT image, there are two principal blobs that define the upper 22 and lower 24 reflective layers. The CCL filter will yield n blobs and the system will use k biggest blobs, where k<<n and k>2. K blobs are sorted from biggest to smallest.

In order to isolate the upper reflective layer—the region for RNFL analysis—the first blob that has a minimum size (scanning from top to bottom) will define the upper layer 22. Using the blob as a footprint for the upper layer, the system moves laterally across the blob filing in any gaps.

To determine the lower reflective layer (which is not used in RNFL analysis), the system recognizes the second largest remaining blob 24 whose latitude is lower than the largest blob 22. As with the upper layer, the gaps are filled in—moving laterally across the blob.

Figure 4:
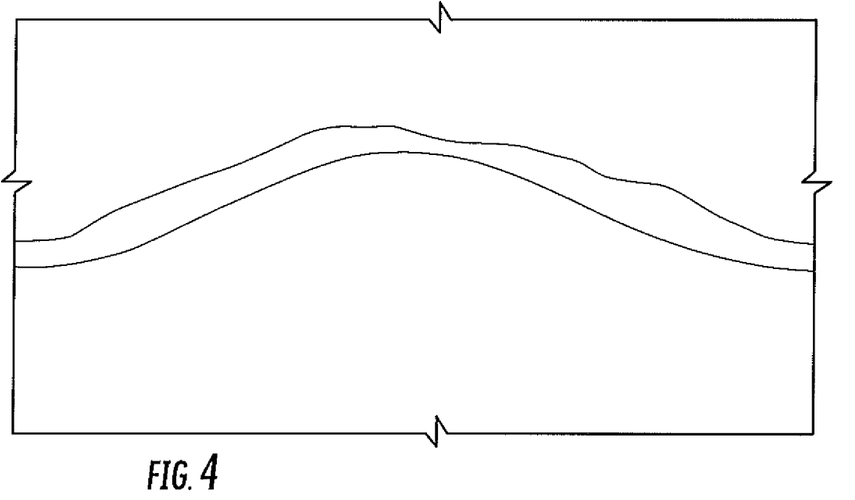
FIG. 4 shows an extracted view of an upper reflective region according to an embodiment of the invention.

After both blobs (i.e. the upper reflective region 22 and the lower reflective region 24) have been so identified, a list of points defining the top border 26 of the upper blob 22 and the top border 28 of the lower blob 24 is produced. This list of points defines the upper reflective layer and is designated as the area of structural analysis. The portions above the upper reflective layer are disregarded. FIG. 4 shows an extracted image of the upper reflective layer.

It will be understood that the list of points may be smoothed by calculating the best approximating polynomials—using the least squares approach. Furthermore, the polynomials may be increased by a small amount (using a defined constant algorithm parameter) to avoid including a piece of the upper layer.

Figure 5:
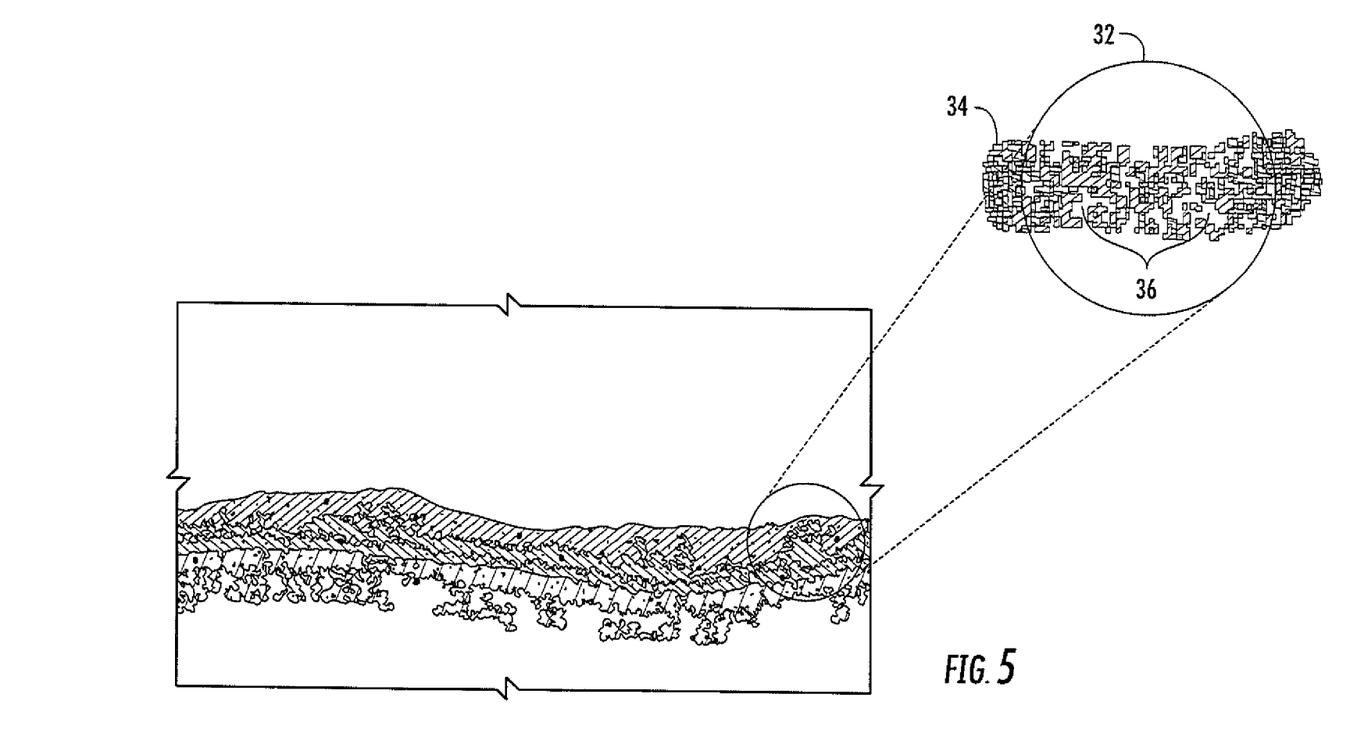
FIG. 5 shows a schematic, enlarged view of a sectoral defect in an RNFL segment according to an embodiment of the invention.

The upper reflective region of an OCT image is comprised of a plurality of dots (best shown in the enlarged portion of FIG. 5). Having identified the upper reflective region—the area for RNFL analysis of the OCT image (or a portion thereof), the system reverts to the original OCT image (stored in digital memory and saved in any of various file formats, such as JPEG, TIFF, GIFF, PDF, etc. or as raw data derived directly from the OCT device) and performs dot analyses on the region isolated as the upper reflective layer. Using the color image, the software performs a discretization operation before detecting, classifying and counting the various colored dots dispersed throughout the image of the RNFL. Discretization means that a range of possible pixel color values is determined for each color. Preferably, the values are wide-ranging to encompass a large spectrum of similar colors/shades. For example, a range of colors including light pink, dark pink, light red, dark red, maroon . . . will be classified as "red." Similar color ranges are set for the other colors to be detected (e.g. yellow, green and blue). Using such color range rules, the software then analyzes each dot and classifies it as one of four (or more) colors.

For example, for each dot that is detected, the system determines the range in which its pixel values fall. Based on the range of pixel values—the dot will be assigned a color.

In an embodiment of the invention, the software codifies an OCT image into four colors (yellow, red, green, and blue) by discretization. To that end, each color is considered as a trio $<R,G,B>$, where R is red, G is green and B is blue. The four classes (i.e. representative points) are defined as: yellow=$<0,1,1>$, red=$<1,0,0>$, green=$<0,1,0>$ and blue=$<0,0,1>$, wherein a given dot belongs to a given class depending on its distance to this given class. The distance between two 3D points is computed as:

$$D(<a_1,a_2,a_3>, <b_1,b_2,b_3>) = \sqrt{(b_1-a_1)^2 + (b_2-a_2)^2 + (b_3-a_3)^2}$$

In one embodiment of the invention a grayscale OCT image is used for dot analysis. In this embodiment, certain thresholds of pixel values will be associated with different grey tonalities. The software codifies an OCT image into four tonalities by discretization. The software uses the same principle of distance between a given clot and its respective (closer) tonality Once the image is analyzed, the computer tallies the number of each of the various classified dots. The computer compares individual dot tallies to similar tallies from a normative database and derives a score based on the degree of deviation from normal. In embodiments of the invention, the comparison is conducted for a particular analyzed OCT segment and for the entire, global OCT image.

Additionally or alternatively, the computer conducts a ratio analysis to determine a ratio of dots with respect to each other based on the tallies of each of the classified dots. Most preferably, the computer examines the number of cold dots in relation to the number of hot dots.

In one preferred embodiment, the computer assigns a numerical index to describe a relationship between hot and cold dots. The index is expressed as a number between 0 and 1 and it is obtained by dividing a lower number of dots by a higher number of dots. As the number gets closer to 1 it is more likely that a glaucomatous condition is present. That is because in a healthy eye, there are more axons than there are support cells and as a result, there are more hot dots than there are cold dots. However, when axon loss occurs, the ratio of axons to support cells becomes diminished, and consequently—the number of hot dots with respect to cold dots decreases. In a glaucomatous eye, the ratio may be as high "1" in the index described above. In one embodiment of the invention, the determined index is compared to a normal index and a score is generated based on the degree of difference between the determined index and the normal index. A high score indicates a corresponding high degree of spread between a determined index and a normal index and vice versa.

In another preferred embodiment, the ratio analysis is done by summing the individual tallies for all hot dots (i.e. red and yellow dots) and summing the individual tallies for cold dots (i.e. green and blue) and then determining the collective ratio of hot-to-cold dots.

In an embodiment, the ratio analysis is performed on a per-sector basis. In this embodiment, a global OCT image is divided into sectors—each of which is individually analyzed. In a preferred embodiment, a global OCT image is divided into between 12-16 sectors. In one embodiment of the invention, each segment is further divided into superior and inferior sections. Analyses such as absolute number comparisons and ratio determinations are performed on each superior and inferior segment of each sector.

In another embodiment, in addition to or supplemental to the above-mentioned ratio determination, the absolute numbers of each of the different dots are compared to the numbers of corresponding dots stored in a database for normal, healthy OCT results. That is, the computer is programmed with a range of a "normal" distribution of each of the various dots that are found in a healthy symptomatic population. As part of the analysis of OCT images, the computer compares the number of each dot-type with the "normal" number of that particular dot-type. If an absolute number of dots in an analyzed OCT image is not within the "normal" range—then the likelihood that glaucoma exist. In a preferred embodiment of the invention there is a "normal" and "abnormal" range and a "borderline" range therebetween. That is, in a preferred embodiment, there is no hard cut-off between normal and abnormal. Rather, if an absolute number is within a normal range, the system will determine that the RNFL is "normal." If the number is sufficiently far from the normal range (i.e. there is a significant reduction in axon cells) then the system will determine the RNFL to be abnormal. If the number falls anywhere between the extremes, the system will deem the RNFL as "borderline."

In a preferred embodiment, the system will generate a result or indication (such as for example a reading on a display screen or a print-out) based on the comparison described above (i.e. ratio analysis or absolute number comparisons). In a preferred embodiment the computer will generate one of a "normal," "abnormal" and "borderline." Alternatively, the computer will generate a scale of how close to "normal" or "abnormal" an image may be based on a dot analysis. (Note that "dot analysis" and "structure analysis" herein, broadly refers to the method of counting dots dispersed among an OCT image and analyzing the numbers as described herein—either comparing absolute numbers of dots or ratios thereof.)

A clinician will likely want to "follow" a patient with a "borderline" result to determine whether or not a disease progression could be detected. Importantly, with the current invention, a clinician has the benefit of an absolute number to compare to subsequent readings. Moreover, in addition to globally comparing readings, a clinician has the ability to make a segment-by-segment comparison over time. This allows for localized and highly sensitive testing for ocular disease.

FIG. 5 shows an OCT image having a focal defect in one segment thereof. The region of the focal defect is enlarged and surrounded by a circle 32. As shown, within the circled area, there is a diminished dot concentration as compared to the rest of the reflective layer (the area outside the circle 32). As shown, in the unaffected region of the RNFL, dots 34 are tightly packed and abutting one another. However, there are open spaces 36 having no dots (or "black spots" on an OCT image) within the area surrounded by circle 32. Such defects will be identified by the inventive system using sectoralization of the RNFL—in one of the above-described methods. For example, using sectoral analysis, the encircled region will be deemed to be abnormal because there are areas having no dots (or "black spots") and as such the absolute number of dots within that sector is diminished. Such diminished number of dots may be calculated as compared to a normative sector or such number may be calculated as compared to a neighboring sector within the same OCT image.

Additionally or alternatively, the defect shown in FIG. 5 may be detected as a result of ratio analysis. That is, if the areas having no dots 36 are a result of a loss of one particular type of cell (e.g. hot dots), then the ratio of hot dots to cold dots within the encircled sector will be indicative of an abnormality as described above.

It will be understood, that the defect shown in FIG. 5 may also be detected based on a global analysis of the image. That is, the defect may attribute to an overall upset of the normal hot-to-cold dot ration or it might contribute to a diminishment of an absolute number of dots as described above.

In another embodiment of the invention, the ratio and/or absolute number analysis described above is performed on an image of the optic disc (lamina cribosa). An OCT image of the optic disc typically comprises a number (e.g. six) slices that combine to represent the optic disc (in much the same way a pie of pizza is a disc comprised of individual slices).

In a glaucomatous eye, the optic disc reflects light more weakly than does a healthy eye. Such diminished reflectivity translates to fewer hot dots in the OCT image. As reflectivity diminishes, the hot dots become increasingly sparse. In a similar manner to that described above, the system quantifies the number of hot dots present to determine the likelihood of glaucoma existing.

As described, an absolute and relative number of hot dots is determined and compared to a predetermined "normal" range. This comparison is performed on a slice-by-slice basis and on the global image of the optic disc.

Additionally, a ratio determination is performed according to the method described above. Namely, the absolute number of hot dots in relation to the absolute number of cold dots is used to derive an index numeral or score. The score represents the degree of spread between hot and cold dots. The score is used to determine a likelihood that glaucoma exists.

It should be noted that the system and method described herein is not limited for use with retinal images, but rather the inventive system may be used to analyze tissue of any of various body sites. The principals set forth in this disclosure relate, broadly, to the analysis of tissue images by quantifying identifiers that correspond to axonal or other cell types.

The analysis of the OCT image described herein is performed by a computer having specialized software to perform the various operations. The computer used to control operations, execute routines and store data may comprise at least one or more processors and memory storage devices. The computer also may receive a number of inputs and outputs for communicating information externally.

The computer operates under the control of an operating system and software applications, components and programs that execute the routines and systems described herein. In general, the routines executed to implement the embodiments of the invention, whether implemented as part of an operating system or a specific application, component, program, object, module or sequence of instructions is referred to herein as "the system", or "software".

Figure 6:
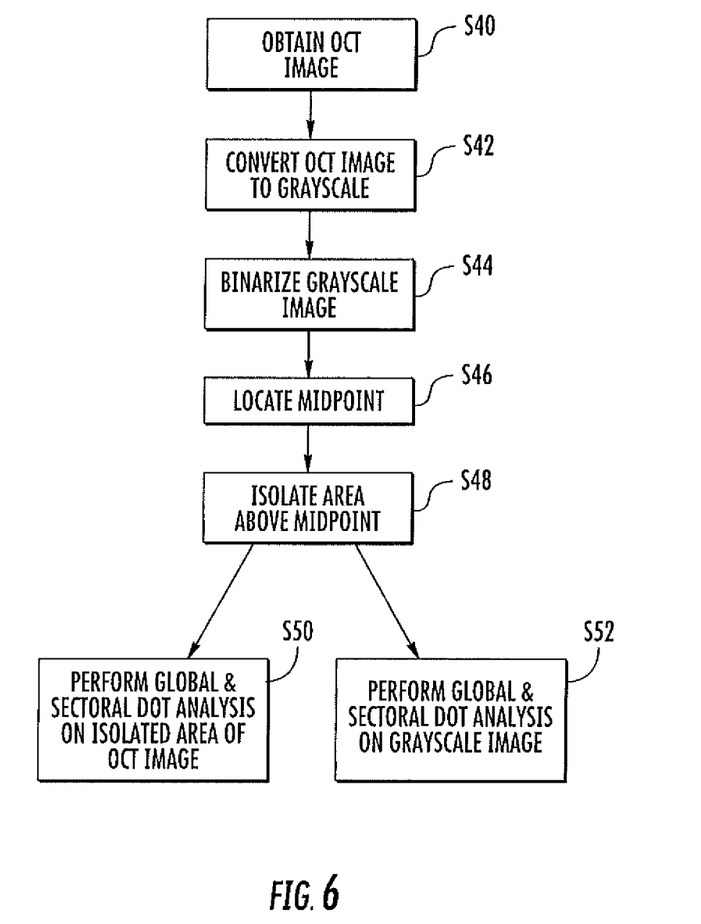
FIG. 6 is a flow chart showing steps of performing dot analysis of an OCT image according to an embodiment of the invention.

FIG. 6 shows a flow chart showing some of the steps performed by the software according to an embodiment of the invention. At step 40, (noted as "S40") an OCT image is obtained in a manner well known in the art. The OCT image is then converted by the software to grayscale S42 and binarized S44. The software then locates the midpoint S46, for example, using the method describe above and the area thereabove is isolated for analysis S48. Once the area of interest is isolated and defined, the system uses the isolated area as a map. That is, the system performs dot analysis on of the original color OCT image S50—but only in the region isolated as described above. Alternatively, the system performs dot analysis on a grayscale OCT image S52.

Figure 7:
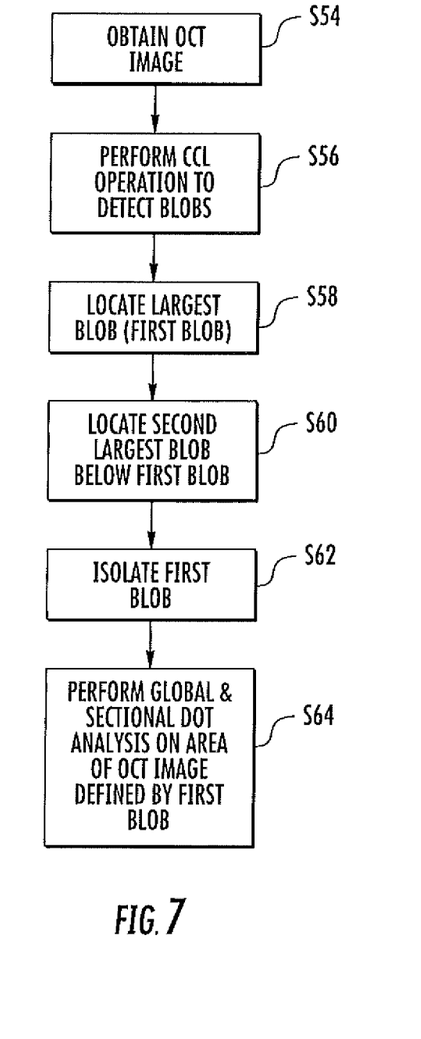
FIG. 7 is a flow chart showing steps of performing dot analysis of an OCT image according to an embodiment of the invention.

FIG. 7 shows a flow chart of the steps performed by the software in another embodiment of the invention. At S54 an OCT image is obtained. Thereafter, the system performs a CCL operation to detect blobs S56. The biggest blob is then selected S58 from a set of blobs detected in S56. A second largest blob is then detected S60—also from the set of blobs detected in S56. The first blob is isolated S62 as the upper reflective layer. Dot analysis is then performed S64 on the region defined by the first blob in the OCT image.

The system described herein may be similarly used to analyze OCT images of any of various tissue types from different body sites. For example, the use of OCT to visualize arterial walls is known in the art. However, in addition to visualizing arteries, the inventive system allows clinician to quantify plaque and/or various cell types associated with cardiac disease. In the area of neurology, the inventive system could be used, in combination with OCT, to quantify nerve cell loss associated with multiple sclerosis or any other neuro-ophthalmic disease. In the field dentistry, the invention may be used to quantify enamel or other tissue structures in an OCT image.

It will be understood by those of ordinary skill in the art that the current invention is not limited to the medical/biological field. Rather, the invention could be utilized to quantify the contents of layers that comprise any OCT image. For example, OCT has shown to accurately detect discrete pigment layers in a painting. The current invention could be utilized to quantify various paints/pigments in the identified layers.

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A system for analyzing an OCT image to detect abnormalities, comprising:
    an OCT image and stored in digital memory, said OCT image comprising at least an upper reflective layer and a lower reflective layer, said OCT image further comprising dots;

a computer with at least one processor and at least one memory storing a software configured to isolate at least a portion of said upper reflective of said OCT image as an area for dot analysis;

said software configured to perform a discretization operation, said discretization operation determining different ranges of pixel values, each of said ranges corresponding to a different color;

said software configured to assign a color to dots in said upper reflective layer of said OCT image, said assignment of color based on a determined range of pixel values; and said software configured to count said dots which were assigned a color.

2. The system of claim 1, wherein said software configured to isolate at least a portion of said upper reflective layer performs the steps of:

converting said OCT image to a grayscale image;
binarizing said grayscale image;
defining a midpoint in said grayscale image; and
isolating a region above said midpoint.

3. The system of claim 1, wherein said software configured to isolate at least a portion of said upper reflective layer performs the steps of:

performing a blob extraction operation on said OCT image to yield a set of blobs;
selecting a largest blob from said set of blobs;
mapping the region of said largest blob; and
performing dot analysis in a region of said upper reflective layer based on the mapping of said region of said largest blob.

4. The system of claim 1, whereby said software is configured to determine four different ranges of pixels values, each of said different ranges corresponding to a different color.

5. The system of claim 4, whereby said different colors are red, yellow, green and blue.

6. The system of claim 5, further comprising software configured to count said dots to yield an absolute number of each of said four different colored dots.

7. The system of claim 6, whereby said software is configured to compare the said absolute numbers of dots to an absolute number of dots determined for a normal OCT image, said absolute number of dots determined for a normal OCT image being stored in a database.

8. system of claim 7, whereby said software generates a result said result comprising a likelihood of abnormality based on said comparison.

\* \* \* \* \*